United States Patent [19]

Welsh

[11] Patent Number: 4,492,614
[45] Date of Patent: Jan. 8, 1985

[54] CHLORINE DETECTION

[75] Inventor: Lawrence B. Welsh, Evanston, Ill.

[73] Assignee: UOP Inc., Des Plaines, Ill.

[21] Appl. No.: 512,298

[22] Filed: Jul. 8, 1983

[51] Int. Cl.³ .......................................... G01N 27/58
[52] U.S. Cl. .................. 204/1 T; 204/421; 204/427
[58] Field of Search .............. 204/1 T, 1 S, 1 B, 421, 204/424, 426, 427

[56] References Cited

U.S. PATENT DOCUMENTS

| | | | |
|---|---|---|---|
| 2,870,067 | 1/1959 | Baker et al. | 204/1 B |
| 3,761,377 | 9/1973 | Mang | 204/195 R |
| 3,969,209 | 7/1976 | Mueller | 204/195 R |
| 4,107,018 | 8/1978 | Bode et al. | 204/427 |
| 4,199,425 | 4/1980 | Sinkevitch | 204/429 |
| 4,265,714 | 5/1981 | Nolan et al. | 204/426 X |
| 4,267,023 | 5/1981 | Frant et al. | 204/1 T |

FOREIGN PATENT DOCUMENTS 695474 10/1964 Canada .................. 204/1 B
1798446 6/1973 Fed. Rep. of Germany ...... 204/1 B

OTHER PUBLICATIONS

Solid State Ionics (1981), North-Holland Publishing Company, pp. 385-388, "Ionic Conductivity of $SnCl_2$" by Kimura and Niizeki.
NASA CR-144954, "Development of a Thin Film Solid State Gaseous HCl Sensor", (North Carolina State University).
Analytical Chemistry, vol. 50, No. 7, Jun. 1978, pp. 965-967, "Detection of HCl Gas in Ambient Air with a Coated Piezoelectric Quartz Crystal", Hlavay and Guilbault.

Primary Examiner—G. L. Kaplan
Assistant Examiner—Nam X. Nguyen
Attorney, Agent, or Firm—James R. Hoatson, Jr.; Richard J. Cordovano; William H. Page, II

[57] ABSTRACT

Apparatus and method for detecting and measuring chloride ion and therefore dissociable chlorine compounds using a solid electrolyte concentration cell. Applicable only to gaseous samples.

12 Claims, 3 Drawing Figures

CHLORINE DETECTION

BACKGROUND OF THE INVENTION

This invention relates to electrochemical measurement and detection. More specifically, it relates to the use of a solid electrolyte in detecting the presence of the element chlorine and measuring the quantity present.

The use of solid electrolyte sensors for detecting oxygen, particularly in automotive exhaust gases, is well known. The present invention utilizes similar basic principles for detecting chlorine. The Nernst equation describes the behavior of sensing devices using solid electrolytes. When two media with different partial pressures, $P_1$ and $P_2$, of a particular substance present in both media are separated by a solid electrolyte (ionic conductor) and conducting electrodes are attached to both sides of the ionic conductor, an EMF is generated which is related to the partial pressures as follows:

$$EMF = \frac{RT}{nF} \ln \frac{P_2}{P_1},$$

where R is the gas constant, T is the absolute temperature, F is the Faraday constant, and n is the number of electrons per molecule of product from the overall cell reaction. If the system described by the above equation behaves non-ideally, the partial pressures must be replaced by fugacities. Another factor which may need to be considered in regard to a particular system is the rate of dissociation to form the ions which pass through the solid electrolyte. This may be a limiting factor to the transfer of ions through the electrolyte. The rate of dissociation can be calculated by means of the equilibrium constant for the dissociation reaction.

There is a need for improved methods and apparatus to detect chlorine, particularly in the area of petroleum refining, where the amount of chlorine present may be critical. For background information relating to the present invention, reference may be made to the book *Solid Electrolytes and Their Applications*, edited by Subbarao, Plenum Press, 1980.

INFORMATION DISCLOSURE

In an article in *Solid State Ionics*, (p. 385, 1981, North-Holland Publishing Company), Kimura and Niizeki reported that stannous chloride is an ionic conductor. They noted that to obtain accurate ionic conductivity measurements, account must be taken of its tendency to be oxidized and its hygroscopic character.

U.S. Pat. Nos. 3,969,209 (Mueller) and 3,761,377 (Mang) deal with methods and apparatus for electrochemical detection of chloride ion using wet chemistry. An integral dosimeter for HCl using reaction with silver is described in U.S. Pat. No. 4,267,023 (Frant et al.). NASA CR-144954 reports on research done at North Carolina State University for the purpose of developing a gaseous HCl sensor based on surface conductivity of a thin film. In an article in *Analytical Chemistry* (June, 1978, p. 965), Hlavay and Guilbault discuss HCl detection by means of a coated piezoelectric quartz crystal and list other analytical methods for HCl in air.

BRIEF SUMMARY OF THE INVENTION

It is among the objects of the present invention to provide methods and apparatus of detecting chloride ion and therefore dissociable chloride compounds in order to indicate the presence or absence of these substances and, where desired, provide quantitative information on the amount present. A particular object is to provide a chlorine leak detector. Another particular object is to provide an instrument for measuring concentrations of chlorine.

The invention utilizes a concentration cell whose electrolyte is a chloride ion conducting material selected from a group consisting of stannous chloride, barium chloride, and lead chloride. An eleaent comprising electrolyte is mounted in a sample cell having a sample gas chamber and a reference gas chamber. The sample gas chamber contains the gas sample of interest, which must include a component capable of dissociating to form chloride ions. In the other chamber is a reference gas whose composition is known. The element comprising the electrolyte must be substantially imporous so that the two gases will not mix by diffusing through it. A catalytic agent for promotion of dissociation to form chloride ions is in intimate contact with the electrolyte element on the sample gas side. Catalytic agent is provided in a like manner on the other side. Electrodes for forming electrical contact and transferring electrons to and from an external circuit are provided on each side of the electrolyte in intimate contact with catalytic agent and therefore with the electrolyte element. The cell EMF is measured across these electrodes and provides an indication of the presence of chlorine in the sample gas and/or a quantitative measure of the amount of chlorine present. The magnitude of EMF produced is generally in accordance with the parameters discussed above: the Nernst equation and, where applicable, the dissociation equilibrium constant. However, required practice in measuring concentration is to periodically calibrate the measuring apparatus by use of samples whose composition is known. Thus, exact adherence to theoretical relationships is not required of commercially used methods and apparatus. The primary commercial requirement is repeatability.

The catalytic agent may be platinum, palladium, or alloys thereof. The catalytic agent may be electrically conductive, so that one substance may serve as both catalyst and electrode. The form of the electrolyte element may require that gas which contacts it be dry. Where temperature of the sample gas is too high or low for effective detection, it may be adjusted before the gas is contacted with the electrolyte element. It may be necessary to adjust the concentration, in a known manner, of gas contacting the electrolyte element in order to achieve effective detection. The electrolyte element may contain a dopant, such as potassium chloride.

DETAILED DESCRIPTION OF THE INVENTION

It will be helpful in gaining an understanding of the invention to examine initial proof of principle experimentation. The information presented in regard to this experimentation is not meant to limit the scope of the invention in any way.

An electrolyte element was fabricated of anhydrous stannous chloride. Material labeled 98% pure $SnCl_2$ was crushed to powder with a mortar and pestle in a glove box containing a dry nitrogen atmosphere. 5.23 Grams of a $-200$ mesh sieve fraction of this powder was placed in a 25.4 mm diameter cylindrical die and pressed at a ram pressure of 55.2 MPa (8000 lbs/in.$^2$). The wafer removed from the die was 2.97 mm thick. The geometric density of the wafer was 3.48 g/cm$^3$, which is 88% of the handbook value. Hot gold wire (0.254 mm diameter) was fused into the surface of each side of the wafer to serve as electrical leads. Platinum was deposited to a thickness of about 800 angstroms onto a central area 9.5 mm in diameter on each side of the wafer and on top of the gold wire fused into the pressed powder surfaces. This was accomplished by using a Hummer II sputter deposition system supplied by Technics Co. There are many alternative methods which could have been used to form the electrodes, such as thin film deposition or deposition by means of an ink.

Figure 1:
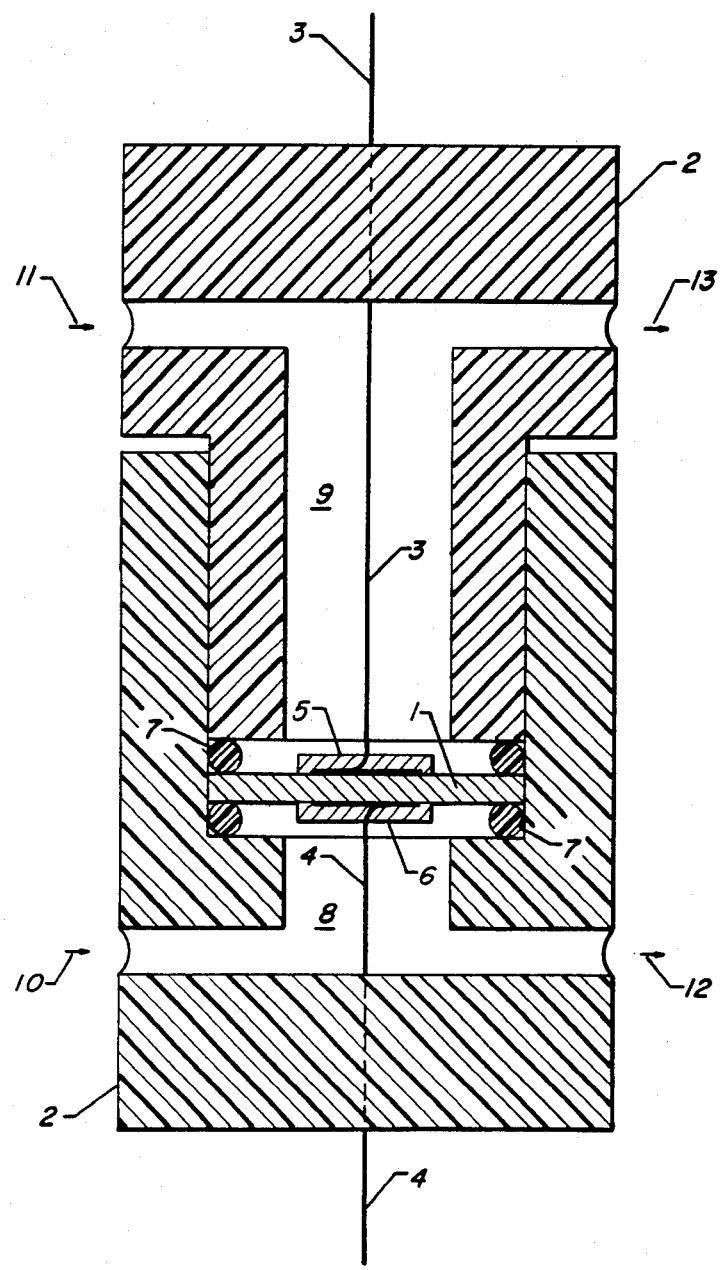
FIG. 1 is a schematic representation, in cross-section, of the test sensor used in initial proof of principle experimentation. The drawing is not to scale.

Referring to FIG. 1, electrolyte element 1 was mounted in test fixture 2, which may also be referred to as a sample cell. Gold wire leads 3 and 4 extended from either side of electrolyte element 1 out of the test fixture through means for sealing against gas leakage (not shown). Leads 3 and 4 were connected to EMF detection means (not shown). Platinum deposits 5 and 6 served as electrodes and catalytic agent to promote dissociation and re-association. Electrolyte element 1 was sealed into test fixture 2 by O-rings 7 so that there were no gas leakage paths between test gas chamber 8 and reference gas chamber 9. Tubing (not shown) was connected at gas inlets 10 and 11 to provide gas flow into chambers 8 and 9 and was also connected to gas outlets 12 and 13 to conduct gas away from the chambers. Gas cylinders and gas flow control apparatus (not shown) were used to provide gas to test the sensor of fixture 2 in accordance with the herein described experiments. Test fixture 2 was placed in a thermostatically controlled electric oven so that tests could be run at controlled temperatures.

Figure 2:
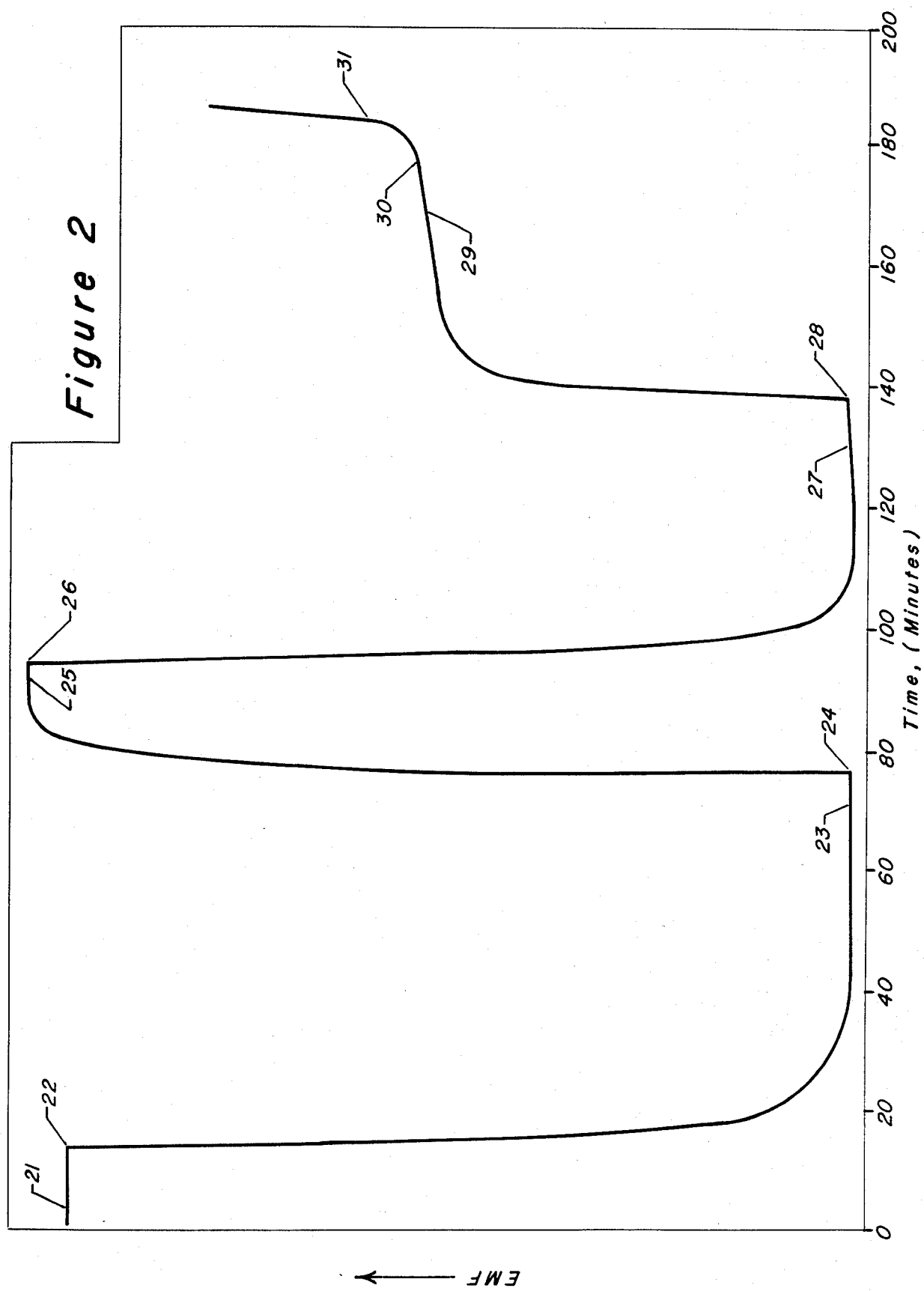
FIG. 2 depicts a portion of the results obtained when gas streams comprising chlorine were passed through the test sensor shown in FIG. 1. It is a reproduction of the tracing of a strip chart recorder. EMF developed in the test sensor is plotted against time.

Two cylinders of helium gas with chlorine gas added were purchased and used as a source of supply for gas passed through test fixture 2. One cylinder was labeled as containing 105 ppm by volume of chlorine and the other as containing 950 ppm. Gas flows from the two cylinders were alternated between test gas chamber 8 and reference gas chamber 9. Referring to FIG. 2, the effect of alternating or switching the gas flows can be seen at points 22, 24, and 26. The portions of the curve designated by 21, 23, 25, and 27 indicate that the system was approaching equilibrium before the gas streams were switched. At point 28, instead of switching the 105 and 950 ppm streams, 950 ppm gas was passed through both chambers at the same time. The portion of the curve at point 29 shows rate of change of EMF decreasing after the rapid change initiated by the concentration change at point 28. Point 30 indicates the effect of a change in temperature. At point 31, flow of the two different gases was resumed. The difference in EMF between the highest and lowest points on the curve of FIG. 2 was 111 millivolts, demonstrating that the EMF produced is in an easily measurable range. Reproducibility of results is shown by the two sets of peaks. The variation in the lower set was less than 1 mv. The difference between the two high peaks was greater (about 5 mv); however, this magnitude of variation is to be expected in preliminary experimentation of this type. Possible reasons for the variation include variation in temperature of the test fixture and exposure history of the electrolyte element. Note that exposure history of the element used included exposure to HCl in He as well as the varying concentrations of $Cl_2$. Other potential problems could be open channel porosity, electronic conduction through the sensor element, and asymmetry in catalyst performance. The response to concentration change was quite satisfactory, as can be seen by the sharpness of the corners as denoted by 22, 24, 26, 28, and 31. Oven temperature for the time period ending at point 30 was 230° F. The EMF response was qualitatively Nernstian. Note that the curve was starting to level off at point 29, where the same gas was flowing on both sides of electrolyte element 1 and that the EMF started to change upon a temperature change. The concentration change superimposed on the temperature change caused the sharp corner at point 31. Calculations made using the data collected from this and other runs with chlorine show that the average voltage response is about 115% of that predicted by the Nernst equation. This is surprisingly good agreement, though quantitative agreement is not necessary to the operation of the invention.

Figure 3:
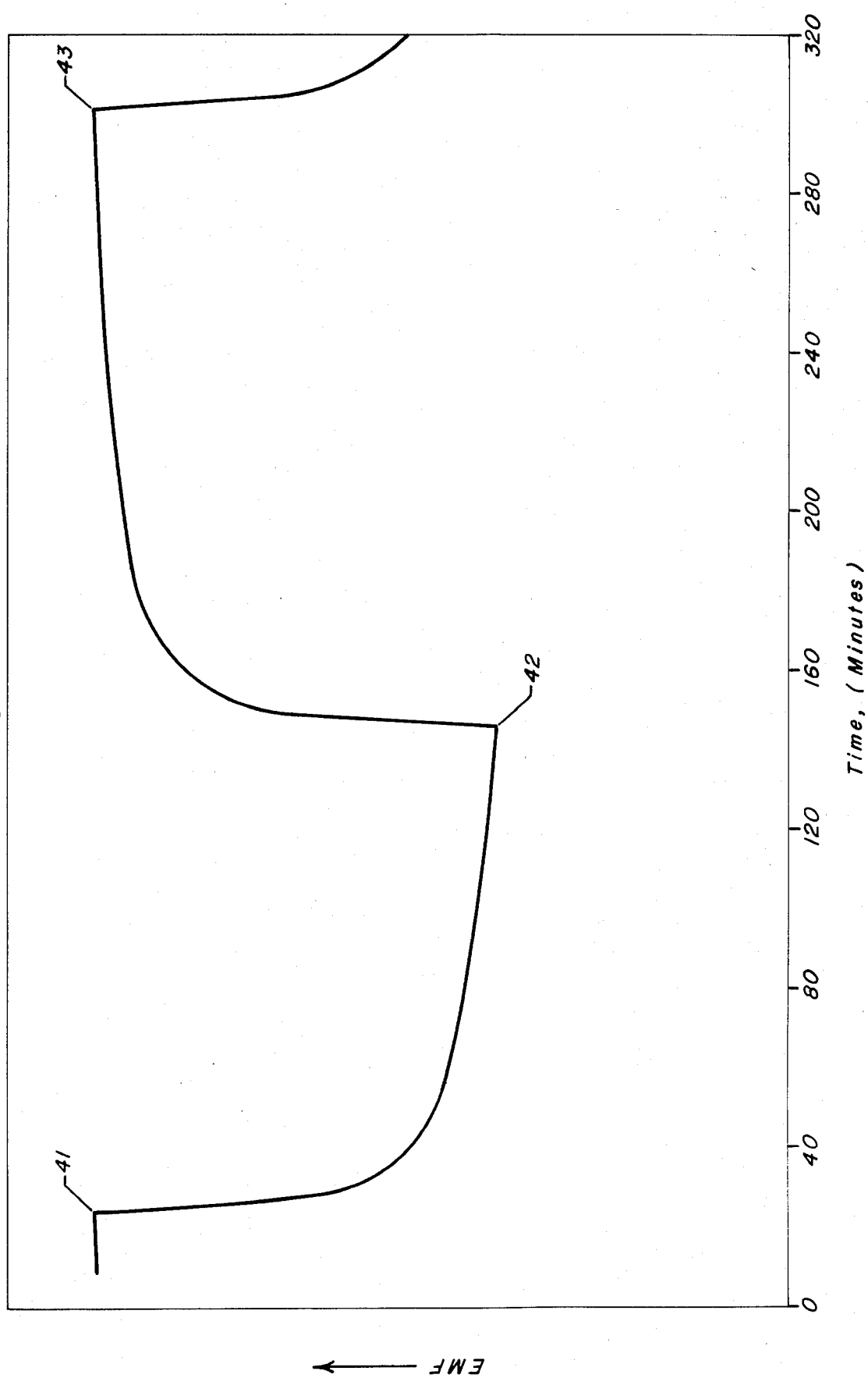
FIG. 3 is similar to FIG. 2 but depicts results when gas streams comprising HCl were passed through the test sensor.

Hydrogen chloride gas in helium was also tested in the same manner. The two gases used consisted of 9.2 and 924 ppm by volume of HCl in He. Points 41, 42, and 43 of FIG. 3 show the effects of switching the gas streams between chambers of the test sensor. The difference between the high points and low point of FIG. 3 was 82 mv. Oven temperature was 230° C. As related above in the $Cl_2$ experimentation, qualitative Nernstian response was observed and quantitative response differed from that predicted by the Nernst equation. The actual average response was about 20% of the predicted response.

The electrolyte element used in the above-described testing was fabricated by simple means readily at hand. A better method may be to melt the stannous chloride, or other material, and form the element in a mold. Holding the temperature for a period of time at a value just below the melting point would promote the growth of large crystals. Those skilled in the art will perceive other methods of forming an electrolyte element, in wafer form or as a thin film or thin film layer. Additional substances, or dopants, may be added to the chloride ion conductive materials of this invention in order to obtain desirable properties of the electrolyte element. For example, a potassium chloride dopant will improve ionic conductivity.

As is common in many analysis instruments, the sample gas provided to a sensor may require conditioning in order to achieve effective detection. Of course, any particulate matter and liquid droplets are removed. The extent of conditioning depends on the particular gas involved and its state. For example, an extremely hot gas must be cooled to a sufficiently low temperature so as not to degrade the apparatus by melting sensor components, including the electrolyte element. A relatively cold gas may need to be heated to a temperature which promotes a reasonable response time of the apparatus. A requirement for heating was demonstrated in a proof of principle experiment accomplished in the same manner as described above except that the temperature was 22° C. instead of 230° C. At this temperature, the time required for the EMF to reach its equilibrium value would be considered unduly long for most applications. Response time in experiments at 160° C. was more reasonable for most applications. It should be noted that response time is dependent upon thickness of the electrolyte element in addition to temperature. Water vapor is often removed from a sample gas stream. The electrolyte element used in the experimentation described herein was not suitable for exposure to water vapor. Other sample-conditioning techniques may be required. For example, in a situation where the concentration of chloride ion is extremely large and capable of saturating the apparatus, the sample may be diluted by addition of a known amount of inert gas. The actual concentration of undiluted sample can then easily be calculated.

A detector may take many forms. A portable battery-operated unit may be used as a "sniffer" to detect the presence in the atmosphere of a particular gas due to leakage from a closed system. A detector may be permanently mounted in a particular location to detect leaks. When conditioning is not required, a detector may be fabricated for insertion directly into a process pipeline. When a gas sample must be conditioned, a small sidestream may be withdrawn from a process pipeline on a continuous or intermittent basis and passed through a sample gas chamber. A quantity of reference gas may be sealed into a reference gas chamber instead of providing a continuous flow. The reference gas may be replaced by a solid comprising a substance which exhibits a chlorine activity which is constant as chloride ion is transferred across the electrolyte element. A solid reference may be a metal chloride, such as the chlorides of aluminum, lithium, copper, and sodium. While the presence of chlorine in the reference material is the preferred mode of operation, it is not required; a voltage will be generated in the absence of chlorine. Without chlorine, the response will not be Nernstian. However, adherence to a particular relationship is not required.

As used herein, the term "detection" includes not only sensing presence or absence of the detected substance, but measurement of the amount of substance present, either in order of magnitude or exact aaounts. Gas sample refers to any portion of a gas which is the subject of detection. Sample cell refers to a housing or fixture which holds an electrolyte element and other required components. Sensor is a general term denoting sensing apparatus. Electrolyte element refers to an ion conducting substance suitable for use as an electrolyte in the concentration cell of this invention which has been formed into a particular physical entity, either with or without additional substances, for use in the invention. Where an electrolyte element surface is referred to as exposed to a gas or gas chamber, such reference does not preclude the presence of catalytic agent and electrodes at or covering the surface. Gas may diffuse through covering material. Sample gas chamber refers to any space in which gas which is the subject of detection exists. For example, a sample cell can form a part of a pipeline wall such that the gas flowing in the pipeline is the sample gas and the pipeline is the sample gas chamber. The term "gas" is used herein to include vaporized liquids regardless of boiling point characteristics of the substance. Chlorine refers to chlorine in chemical combination with other substances and/or in an uncombined form.

It is believed that the principles of the present invention are also applicable to detection of the other halides.

I claim as my invention:

1. An apparatus for detection, in a gas sample containing a concentration of chlorine which is capable, in the presence of a catalytic agent, of dissociating to yield chloride ions, comprising:
   (a) a sensor housing comprising a sample gas chamber and a reference gas chamber;
   (b) an imporous solid electrolyte element partition separating said sample gas and said reference gas chamber having a first surface in common with said sample gas chamber and a second surface in common with said reference gas chamber, wherein said solid electrolyte element partition comprises a chloride ion conducting material selected from the group consisting of stannous chloride, barium chloride and lead chloride;
   (c) a catalytic agent selected from the group consisting of platinum, palladium and alloys of platinum and palladium effective to promote dissociation and combination of said chloride ions in contact with said first surface in common with said sample gas chamber;
   (d) a catalytic agent selected from the group consisting of platinum, palladium and alloys of platinum and palladium effective to promote dissociation and combination of said chloride ions in contact with said second surface in common with said reference gas chamber; and,
   (e) means for forming an electrical connection in operative contact with said catalytic agent which is in contact with said first surface and said catalytic agent which is in contact with said second surface.

2. The apparatus of claim 1 further including means for removing substantially all water in the gas sample before it contacts said imporous solid electrolyte element.

3. The apparatus of claim 1 further including means to adjust the operating temperature of said sample gas chamber.

4. The apparatus of claim 1 further including means to adjust the concentration of chlorine in the gas sample before it contacts said imporous solid electrolyte element.

5. The apparatus of claim 1 further characterized in that said imporous solid electrolyte element also comprises a dopant.

6. The apparatus of claim 5 further characterized in that said dopant is potassium chloride.

7. A method for detection, in a gas sample containing a concentration chlorine which is capable, in the presence of a catalytic agent, of dissociating to yield chloride ions, comprising contacting said gas sample with a first surface of an imporous solid electrolyte element and detecting an EMF between means for forming electrical connection with two separate portions of a catalytic agent effective to promote dissociation and combination, where a catalytic agent selected from the group consisting of platinum, palladium and alloys of platinum and palladium is in contact with said first surface and a catalytic agent selected from the group consisting of platinum, palladium and alloys of platinum and palladium is in connection with a second surface of said imporous solid electrolyte element, which element isolates said gas sample from a reference gas and has said second surface exposed to said reference gas, said element comprising a chloride ion conducting material selected from the group consisting of stannous chloride, barium chloride, and lead chloride.

8. The method of claim 7 further characterized in that said gas sample contains hydrogen chloride.

9. The method of claim 7 further characterized in that said gas sample contains elemental chlorine.

10. The method of claim 7 further characterized in that water is removed from said sample before the sample contacts said imporous solid electrolyte element.

11. The method of claim 7 further characterized in that the concentration of chlorine in the gas sample is adjusted before the gas sample contacts said imporous solid electrolyte element.

12. The method of claim 11 further characterized in that the concentration of said chlorine in said gas sample is adjusted to be between approximately 10 ppm and 1000 ppm by volume.

* * * * *